US012378514B2

(12) United States Patent
Lee

(10) Patent No.: US 12,378,514 B2
(45) Date of Patent: Aug. 5, 2025

(54) MATERIAL TRANSFER DEVICES AND RELATED SYSTEMS AND METHODS

(71) Applicant: PBS BIOTECH, INC., Camarillo, CA (US)

(72) Inventor: Chanyong Brian Lee, Newbury Park, CA (US)

(73) Assignee: PBS BIOTECH, INC., Camarillo, CA (US)

( * ) Notice: Subject to any disclaimer, the term of this patent is extended or adjusted under 35 U.S.C. 154(b) by 801 days.

(21) Appl. No.: 17/318,738

(22) Filed: May 12, 2021

(65) Prior Publication Data

US 2021/0355425 A1  Nov. 18, 2021

Related U.S. Application Data

(60) Provisional application No. 62/704,473, filed on May 12, 2020.

(51) Int. Cl.
*C12M 1/00* (2006.01)
*C12M 1/12* (2006.01)
*C12M 1/34* (2006.01)
*C12N 1/00* (2006.01)

(52) U.S. Cl.
CPC ............ *C12M 29/18* (2013.01); *C12M 23/58* (2013.01); *C12M 25/14* (2013.01); *C12M 41/46* (2013.01); *C12N 1/00* (2013.01)

(58) Field of Classification Search
CPC ...... C12M 29/18; C12M 23/58; C12M 25/14; C12M 41/46; C12M 47/04; C12M 29/04; C12N 1/00
See application file for complete search history.

(56) References Cited

U.S. PATENT DOCUMENTS

| 5,518,528 A | 5/1996 | Tom et al. |
| 5,704,965 A | 1/1998 | Tom et al. |
| 5,704,967 A | 1/1998 | Tom et al. |

(Continued)

FOREIGN PATENT DOCUMENTS

| DE | 102015109148 B3 | 5/2016 |
| EP | 2692853 A1 | 2/2014 |

(Continued)

OTHER PUBLICATIONS

International Application No. PCT/US2021/031953, International Search Report and Written Opinion, mailed Aug. 17, 2021.

(Continued)

*Primary Examiner* — Liban M Hassan
(74) *Attorney, Agent, or Firm* — MARSHALL, GERSTEIN & BORUN LLP

(57) ABSTRACT

Material transfer devices and related systems and methods are disclosed. In accordance with an example, a material transfer device includes a housing including a first housing portion and a second housing portion and a screen. The first housing portion includes a first inlet port, a first outlet port, and a first transfer opening. The second housing portion has a second inlet port, a second outlet port, and a second transfer opening. The first transfer opening is disposed adjacent to and in communication with the second transfer opening. The screen is disposed between the housing portions adjacent to the first and second transfer openings.

16 Claims, 7 Drawing Sheets

(56) References Cited

U.S. PATENT DOCUMENTS

| | | |
|---|---|---|
| 5,837,027 A | 11/1998 | Olander et al. |
| 5,851,270 A | 12/1998 | Olander |
| 5,875,921 A | 3/1999 | Osgar et al. |
| 5,917,140 A | 6/1999 | Tom |
| 5,935,305 A | 8/1999 | Tom et al. |
| 5,964,254 A | 10/1999 | Jackson |
| 6,029,718 A | 2/2000 | Jackson et al. |
| 6,047,744 A | 4/2000 | Jackson |
| 6,077,356 A | 6/2000 | Bouchard |
| 6,089,027 A | 7/2000 | Wang et al. |
| 6,101,816 A | 8/2000 | Wang et al. |
| 6,132,492 A | 10/2000 | Hultquist et al. |
| 6,192,919 B1 | 2/2001 | Jackson et al. |
| 6,199,599 B1 | 3/2001 | Gregg et al. |
| 6,204,180 B1 | 3/2001 | Tom et al. |
| 6,206,240 B1 | 3/2001 | Osgar et al. |
| 6,296,025 B1 | 10/2001 | Gregg et al. |
| 6,296,026 B1 | 10/2001 | Gregg et al. |
| 6,343,476 B1 | 2/2002 | Wang et al. |
| 6,406,519 B1 | 6/2002 | Tom et al. |
| 6,435,229 B1 | 8/2002 | Noah et al. |
| 6,447,584 B1 | 9/2002 | Kishkovich et al. |
| 6,457,494 B1 | 10/2002 | Gregg et al. |
| 6,540,819 B2 | 4/2003 | Tom et al. |
| 6,610,128 B2 | 8/2003 | Kishkovich |
| 6,637,475 B2 | 10/2003 | Noah et al. |
| 6,698,619 B2 | 3/2004 | Wertenberger |
| 6,716,271 B1 | 4/2004 | Arno et al. |
| 6,740,147 B2 | 5/2004 | Kishkovich et al. |
| 6,743,278 B1 | 6/2004 | Carruthers |
| 6,761,753 B2 | 7/2004 | Kishkovich et al. |
| 6,857,447 B2 | 2/2005 | Olander et al. |
| 6,879,876 B2 | 4/2005 | O'Dougherty et al. |
| 6,880,592 B2 | 4/2005 | Gregg et al. |
| 6,921,062 B2 | 7/2005 | Gregg et al. |
| 6,939,394 B2 | 9/2005 | Carruthers |
| 6,942,123 B2 | 9/2005 | Wertenberger |
| 7,025,234 B2 | 4/2006 | Priebe et al. |
| 7,067,616 B2 | 6/2006 | Alberg |
| 7,152,781 B2 | 12/2006 | O'Dougherty et al. |
| 7,153,425 B2 | 12/2006 | Stankowski et al. |
| 7,160,719 B2 * | 1/2007 | Nyberg .............. C12N 5/067 435/325 |
| 7,163,237 B2 | 1/2007 | Niermeyer et al. |
| 7,172,096 B2 | 2/2007 | O'Dougherty |
| 7,188,644 B2 | 3/2007 | Kelly et al. |
| 7,296,582 B2 | 11/2007 | Campbell et al. |
| 7,328,716 B2 | 2/2008 | Olander et al. |
| 7,335,721 B2 | 2/2008 | Alberg |
| 7,350,821 B2 | 4/2008 | Campbell et al. |
| 7,370,791 B2 | 5/2008 | O'Dougherty et al. |
| 7,378,017 B2 | 5/2008 | Stankowski et al. |
| 7,455,719 B2 | 11/2008 | Carruthers |
| 7,469,932 B2 | 12/2008 | Niermeyer et al. |
| 7,487,956 B2 | 2/2009 | Gregg et al. |
| 7,494,530 B2 | 2/2009 | Carruthers |
| 7,501,010 B2 | 3/2009 | Brestovansky et al. |
| 7,556,244 B2 | 7/2009 | Gregg et al. |
| 7,614,421 B2 | 11/2009 | Olander et al. |
| 7,664,568 B2 | 2/2010 | O'Dougherty et al. |
| 7,702,418 B2 | 4/2010 | O'Dougherty et al. |
| 7,705,382 B2 | 4/2010 | Van Buskirk et al. |
| 7,747,344 B2 | 6/2010 | O'Dougherty et al. |
| 7,815,805 B2 | 10/2010 | Niermeyer et al. |
| 7,828,274 B2 | 11/2010 | Gregg et al. |
| 7,838,329 B2 | 11/2010 | Hunks et al. |
| 7,922,791 B2 | 4/2011 | Grayfer et al. |
| 7,943,204 B2 | 5/2011 | Olander et al. |
| 8,002,880 B2 | 8/2011 | Carruthers |
| 8,008,117 B2 | 8/2011 | Hunks et al. |
| 8,062,965 B2 | 11/2011 | Kaim et al. |
| 8,138,071 B2 | 3/2012 | Kaim et al. |
| 8,150,549 B2 | 4/2012 | O'Dougherty et al. |
| 8,227,714 B2 | 7/2012 | Rajagopal et al. |
| 8,237,134 B2 | 8/2012 | Kaim et al. |
| 8,389,068 B2 | 3/2013 | Olander et al. |
| 8,399,865 B2 | 3/2013 | Kaim et al. |
| 8,501,976 B2 | 8/2013 | Baum |
| 8,506,689 B2 | 8/2013 | Brestovansky et al. |
| 8,539,781 B2 | 9/2013 | Carruthers et al. |
| 8,598,022 B2 | 12/2013 | Kaim et al. |
| 8,617,972 B2 | 12/2013 | Zheng |
| D702,128 S | 4/2014 | Ware et al. |
| 8,779,383 B2 | 7/2014 | Mayer et al. |
| 8,785,889 B2 | 7/2014 | Kaim et al. |
| 8,796,131 B2 | 8/2014 | Jones et al. |
| 8,821,640 B2 | 9/2014 | Cleary et al. |
| 8,849,448 B2 | 9/2014 | O'Dougherty et al. |
| 8,858,685 B2 | 10/2014 | Carruthers |
| 9,004,462 B2 | 4/2015 | Gregg et al. |
| 9,012,874 B2 | 4/2015 | Kaim et al. |
| 9,017,453 B2 | 4/2015 | Petruska et al. |
| 9,031,683 B2 | 5/2015 | Elfstrom et al. |
| 9,062,829 B2 | 6/2015 | Brestovansky et al. |
| 9,067,718 B2 | 6/2015 | Koland et al. |
| 9,070,875 B2 | 6/2015 | Zheng |
| 9,156,020 B2 | 10/2015 | Petruska et al. |
| 9,211,993 B2 | 12/2015 | Tom et al. |
| 9,370,744 B2 | 6/2016 | Petruska et al. |
| 9,376,655 B2 | 6/2016 | Larsen et al. |
| 10,059,915 B2 | 8/2018 | Lee et al. |
| 10,850,279 B2 | 12/2020 | Bores |
| 10,981,117 B2 | 4/2021 | Iyer et al. |
| 2005/0260175 A1 | 11/2005 | Hedrick et al. |
| 2013/0059288 A1 * | 3/2013 | Dankbar .............. C12Q 1/6806 435/2 |
| 2015/0202593 A1 | 7/2015 | Petruska et al. |
| 2016/0030879 A1 | 2/2016 | Petruska et al. |
| 2016/0272943 A1 | 9/2016 | Stone et al. |
| 2017/0342368 A1 | 11/2017 | Matthiesen et al. |
| 2018/0169547 A1 | 6/2018 | Lacey |
| 2022/0145230 A1 | 5/2022 | Kaiser |

FOREIGN PATENT DOCUMENTS

| | | |
|---|---|---|
| EP | 3556839 A1 | 10/2019 |
| JP | 2009-038998 A | 2/2009 |
| JP | 2017523770 A | 8/2017 |
| WO | WO-2009/153425 A2 | 12/2009 |
| WO | WO-2012/057497 A2 | 5/2012 |
| WO | WO-2016/015767 A1 | 2/2016 |
| WO | WO-2017/112455 A2 | 6/2017 |

OTHER PUBLICATIONS

"Hanging Filter Bag", Data Sheet, 2 pp., Sentinel Process Systems, Inc., publicly available before May 12, 2020.
"Microcarrier bead separation and cell harvesting using the Harvestainer large-scale system", ThermoFisher Scientific, 4 pp. Product Brochure (2018).
"Microcarrier Separation System", Product Brochure, 2 pp., Entegris, 2010.
"Microcarrier Filter Bags", Sentinel Process Systems, Inc., downloaded from the Internet at: <https://sentinelprocess.com/hanging-filter-bag.html> publicly available before May 12, 2020.
Harvestainer BioProcess Containers, Product Brochure, 8 pp., ThermoFisher Scientific, 2017.
JM BioConnect®—Make the Connection, Product Brochure, 6 pp. JM BioConnect®, publicly available before May 12, 2020.
Single-use Solutions from Avantor, Avantor Sciences, downloaded from the Internet at: <https://www.avantorsciences.com/pages/en/single-use-solutions> publicly available before May 12, 2020.

* cited by examiner

MATERIAL TRANSFER DEVICES AND RELATED SYSTEMS AND METHODS

RELATED APPLICATION SECTION

This application claims the benefit of and priority to U.S. Provisional Patent Application No. 62/704,473, filed May 12, 2020, the content of which is incorporated by reference herein in its entirety and for all purposes.

FIELD OF THE DISCLOSURE

The present patent relates generally to bioprocessing equipment and, in particular, to material transfer devices and related systems and methods for use with bioprocessing.

BACKGROUND

Biomanufacturing processes for therapeutic cells grown in suspension culture inside single-use bioreactors are being developed for a wide range of cell and gene therapy applications. Depending on their type and properties, many of these therapeutic cells proliferate while clumped together as aggregates, or while attached to the surface of microcarriers (MCs). Accounting for the specific process needs of these cell aggregates or MCs, which are larger and heavier than suspended single cells, is critical for scalable manufacturing of cell and gene therapy products to treat patients with serious diseases indications.

As part of a cell culture process, the liquid medium in which the cell aggregates or MCs are suspended will need to be exchanged, i.e., spent medium removed and fresh medium added. For cell expansion steps, this exchange can be used to replenish nutrients and eliminate metabolic waste products. For a multi-step directed differentiation procedure, rapid and efficient medium exchange between each step is critical to remove previously used differentiation factors and thus prevent unwanted heterogeneous differentiation.

There are various known techniques for performing medium exchange during cell expansion or differentiation of therapeutic cells in bioreactors. One common method is to pause agitation and allow all the cell aggregates or MCs to settle by gravity to the bottom of the bioreactor. Once a bed of settled cell aggregates or MCs is formed, the supernatant of spent medium above the bed of settled cell aggregates or MCs is removed, fresh medium is added, and agitation is restarted to re-suspend the cell aggregates or MCs. There are two potential issues with this settling method. First, the temporary cessation of mixing can lead to cell damage through unwanted agglomeration, nutrient starvation, and deviation of key process parameters such as temperature, pH, and dissolved oxygen levels, especially during the prolonged period of the medium exchange process in a large scale bioreactor. Second, it is difficult to completely remove all the spent medium without losing cells near the bed of settled cell aggregates or MCs, which can result in a carryover of unwanted residual differentiation factors or metabolic wastes in the spent medium. Furthermore, these issues become exacerbated at larger volumetric scales of bioreactors, where the medium exchange process will take a longer time for a greater number of cell aggregates or MCs to settle, and there will also be more medium that needs to be removed and replenished.

Successful large scale manufacturing of therapeutic cells grown on MCs or as cell aggregates has yet to be demonstrated, and the need for enabling manufacturing technologies is becoming more urgent as more therapeutic cell candidates are approaching clinical trials. A potential bottleneck of large scale cell culture processes is the current lack of reliable and robust method for large scale medium exchange, especially for differentiation of pluripotent stem cells (PSCs) grown as suspended aggregates in a bioreactor.

SUMMARY

The disclosed examples relate to material transfer devices and related systems that efficiently filter cells, cell aggregates, and/or associated microcarriers (MCs) from spent medium while reducing stress on the cells during the filtering and/or transferring process. Thus, the disclosed implementations minimize the time that therapeutic cells spend outside of a bioreactor's ideal fluid environment (comprised of nutrients, agitation, temperature, etc.), thereby addressing a current bottleneck for commercial scale manufacturing. The material transfer devices and systems are intended to form aseptic connections to other devices (e.g., bioreactors) used in cell culture processes. This ensures that therapeutic cells remain in a completely closed system throughout the cell culture process, in order to minimize contamination risk from the external environment. Also, the material transfer devices and systems may be automated and provide relatively rapid cycling. As such, the material transfer devices may have a relatively small volume as compared to a bioreactor, while providing medium exchange for larger scale bioreactor volumes.

To do so, the material transfer devices include a housing including first and second housing portions that are separated by a screen and have corresponding first and second ports. The first pair of ports may be used to carry medium containing cell aggregates or microcarriers into and out of the housing, the screen may be used to separate the cell aggregates or the microcarriers from the medium, and the second pair of ports may be used to carry medium without the cell aggregates or the microcarriers into and out of the housing.

As an example, one of the first pair of ports may be used to carry spent medium including cell aggregates or microcarriers into the first housing portion and one of the second pair of ports may be used to carry the spent medium from the housing. Thereafter, the other one of the second pair of ports may be used to carry fresh medium into the housing that passes through the screen and rehydrates the cell aggregates and the microcarriers, and the other one of the first pair of ports may be used to carry the fresh medium suspending the cell aggregates or the microcarriers from the first housing portion. The screen, the housing, and/or the ports may be differently arranged. For example, the screen and/or the housing portions may be parallel relative to a horizontal plane and/or angled relative to the horizontal plane. Moreover, the ports may be differently arranged such that the spent medium may carry downward through the material transfer device or upward through the material transfer device.

In accordance with a first example, a material transfer device includes a housing including a first housing portion and a second housing portion and a screen. The first housing portion includes a first inlet port, a first outlet port, and a first transfer opening. The second housing portion has a second inlet port, a second outlet port, and a second transfer opening. The first transfer opening is disposed adjacent to and in communication with the second transfer opening. The screen is disposed between the housing portions adjacent to the first and second transfer openings.

In accordance with a second example, a method of using a material transfer device including a first housing portion and a second housing portion with a screen disposed between the housing portions where each of the housing portions includes an inlet port, an outlet port, and corresponding fluidic tubes connected to the inlet and outlet ports includes pumping spent medium including cell aggregates or microcarriers through the inlet port of the first housing portion. The method includes filtering the cell aggregates or the microcarriers using a screen and passing the spent medium through the screen and into the second housing portion. The method includes pumping the spent medium out of the outlet port of the second housing portion and pumping fresh medium into the first housing portion or the second housing portion. The method includes resuspending the cell aggregates or the microcarriers. The method includes pumping the fresh medium and suspending the cell aggregates or the microcarriers out of the outlet port of the first housing portion.

In accordance with a third example, a control system for controlling fluid flow through a material transfer device including a first housing portion and a second housing portion with a screen disposed between the housing portions where each of the housing portions includes an inlet port, an outlet port, and corresponding fluidic tubes connected to the inlet and outlet ports, the control system includes a base and a plurality of valves and a plurality of pumps. The base defines a receptacle and adapted to support the material transfer device and the plurality of valves and the plurality of pumps are adapted to control medium flow through each of the inlet ports and the outlet ports of the transfer device.

In accordance with a fourth example, a material transfer device includes a housing and a screen. The housing includes a first housing portion and a second housing portion, where each housing portion includes an inlet port and an outlet port. The screen is disposed between the housing portions. The inlet port of the first housing portion is arranged to flow spent medium including cell aggregates or microcarriers into the first housing portion and the screen is adapted to prevent the cell aggregates or the microcarriers from passing through the screen while allowing the spent medium to pass through the screen, into the second housing portion, and toward the outlet port of the second housing portion. The inlet port of the second housing portion is arranged to flow fresh medium into the second housing portion and the screen is adapted to allow the fresh medium to flow through the screen to resuspend the cell aggregates or the microcarriers within the first housing portion.

In accordance with a fifth example, a material transfer device includes a mesh screen, a first housing portion, and a second housing portion. The first housing portion has a cell inlet and a cell outlet and the second housing portion has a medium outlet and a medium inlet and is coupled to the first housing portion. The mesh screen is disposed between the first housing portion and the second housing portion and is adapted to prevent cell aggregates or microcarriers from passing through the screen and to allow spent medium to pass through the screen and to the fluid outlet. The mesh screen is also adapted to allow fresh medium to pass through the screen and to the cell outlet.

In accordance with a sixth example, a method includes receiving, within a material transfer device, microcarriers or cell aggregates in spent medium from a first bioreactor; retaining the microcarriers or the cell aggregates on a first side of a filter of the material transfer device while flowing the spent medium through the filter in a first direction; reversing the flow through the filter by flowing fresh medium through the filter in a second direction opposite the first direction to resuspend the microcarriers or the cell aggregates in the fresh medium; and flowing the microcarriers or the cell aggregates in the fresh medium out of the material transfer device and to a second bioreactor.

In further accordance with the foregoing first, second, third, fourth, fifth, and/or sixth examples, an apparatus and/or method may further include any one or more of the following examples as well.

In accordance with one example, the first inlet port of the first housing portion is arranged to carry spent medium including cell aggregates or microcarriers into the first housing portion and the screen is adapted to prevent the cell aggregates or the microcarriers from passing through the screen while allowing the spent medium to pass through the screen into the second housing portion and toward the second outlet port of the second housing portion. Moreover, the second inlet port of the second housing portion is arranged to carry fresh medium into the second housing portion and the screen is adapted to allow the fresh medium to flow through the screen to re-suspend the cell aggregates or the microcarriers within the first housing portion.

In accordance with another example, the first outlet port of the first housing portion is arranged to allow the fresh medium suspending the cell aggregates or the microcarriers to flow out of the first housing portion.

In accordance with another example, the screen is a flexible screen defining a plurality of pores to enable flow of material therethrough.

In accordance with another example, the material transfer device further includes a support operably coupled to the housing and disposed between the first and second housing portions and adjacent to the screen to provide structural support for the screen.

In accordance with another example, the support includes at least one of a first support extending across the first transfer opening and a second support extending across the second transfer opening.

In accordance with another example, the first support is coupled to the first housing portion adjacent to the first transfer opening and the second support is coupled to the second housing portion adjacent to the second transfer opening.

In accordance with another example, the support comprises a lattice structure.

In accordance with another example, the first housing portion and the second housing portion are each rigid or semi-rigid structures.

In accordance with another example, the first housing portion and the second housing portion each include or are made of flexible materials.

In accordance with another example, the first housing portion is removably coupled to or integrally formed with the second housing portion.

In accordance with another example, the first housing portion is an upper housing portion and the second housing portion is a lower housing portion.

In accordance with another example, the material transfer device includes a seal at an interface between the first housing portion and the second housing portion.

In accordance with another example, the first inlet port and the first outlet port are centrally disposed in the first housing portion and the second inlet port and the second outlet port are centrally disposed in the second housing portion.

In accordance with another example, the screen is horizontally disposed relative to a horizontal plane when the material transfer device is being used.

In accordance with another example, the first housing portion is a lower housing portion and the second housing portion is an upper housing portion.

In accordance with another example, the first housing portion includes a funnel shape that leads to the first outlet port.

In accordance with another example, the first housing portion further includes an internal barrier that extends across a width of the first housing portion and is adapted to prevent accumulated cell aggregates or microcarriers from covering the first inlet port of the first housing portion.

In accordance with another example, the second outlet port of the second housing portion is adapted to be arranged lower than the second inlet port of the second housing portion.

In accordance with another example, the first inlet port of the first housing portion is arranged relative to the screen to allow the spent medium including the cell aggregates or the microcarriers to flow tangentially along a surface of the screen.

In accordance with another example, the screen and the housing are at an angle relative to a horizontal plane when the material transfer device is being used.

In accordance with another example, the method further includes passing the fresh medium through the screen and into the first housing portion.

In accordance with another example, passing the spent medium through the screen includes passing the spent medium through a first transfer opening of the first housing portion and a second transfer opening of the second housing portion disposed adjacent to and in communication with the first transfer opening.

In accordance with another example, the method includes supporting the screen using a support operably coupled to the housing and disposed between the first and second housing portions.

In accordance with another example, passing the spent medium through the screen includes passing the spent medium through the screen horizontally disposed relative to a horizontal plane.

In accordance with another example, passing the spent medium through the screen includes passing the spent medium through the screen disposed at an angle relative to a horizontal plane.

In accordance with another example, further including the material transfer device disposed on or otherwise mounted on the base.

In accordance with another example, the valves and the pumps are adapted to (1) pump spent medium including cell aggregates or microcarriers through the inlet port of the first housing portion to allow the cell aggregates or the microcarriers to be filtered by the screen and to allow the spent medium to pass through the screen and into the second housing portion; (2) pump the spent medium out of the outlet port of the second housing portion; (3) pump fresh medium into the second housing portion to allow the fresh medium to flow through the screen into the first housing portion to resuspend the cell aggregates or the microcarriers; and (4) pump the fresh medium suspending the cell aggregates or the microcarriers out of the outlet port of the first housing portion.

In accordance with another example, further including a wall coupled to the base and carrying two of the valves and two of the corresponding pumps and the base further carries two of the valves and two of the corresponding pumps.

In accordance with another example, the base includes a first side opposite a second side with each side defining a channel through which at least one fluidic tube is adapted to pass.

In accordance with another example, the control system includes a flow meter adapted to determine a flow rate value of the spent medium entering or exiting the second portion of the housing and the control system is adapted to change a pump rate of the pump pumping the spent medium out of the outlet port of the second housing portion of the transfer device in response to the determined flow rate value satisfying a threshold flowrate valve.

In accordance with another example, the control system includes a user interface adapted to allow input to be received by the control system to control a flow sequence through the transfer device.

In accordance with another example, the valves are pinch valves.

In accordance with another example, the control system includes a heater adapted to heat the material transfer device.

In accordance with another example, the method includes exhausting the spent medium from the material transfer device prior to reversing the flow through the filter by flowing the fresh medium through the filter in the second direction.

In accordance with another example, receiving microcarriers or cell aggregates in the spent medium within the material transfer device from the first bioreactor comprises pumping the microcarriers or the cell aggregates in the spent medium to the material transfer device.

In accordance with another example, receiving microcarriers or cell aggregates in the spent medium within the material transfer device from the first bioreactor comprises flowing the microcarriers or the cell aggregates in the spent medium to the material transfer device based on gravity.

In accordance with another example, receiving microcarriers or cell aggregates in the spent medium within the material transfer device from the first bioreactor comprises flowing the microcarriers or the cell aggregates in the spent medium to the material transfer device based on a pressure differential between the first bioreactor and the material transfer device.

In accordance with another example, further including heating the material transfer device.

In accordance with another example, further including rotating the material transfer device to encourage the microcarriers or the cell aggregates to move away from the screen.

In accordance with another example, the first bioreactor, the material transfer device, and the second bioreactor is a closed system to provide an aseptic environment.

In accordance with another example, the first bioreactor, the material transfer device, and the second bioreactor are aseptically connected as part of a completely closed system.

DETAILED DESCRIPTION

Figure 1:
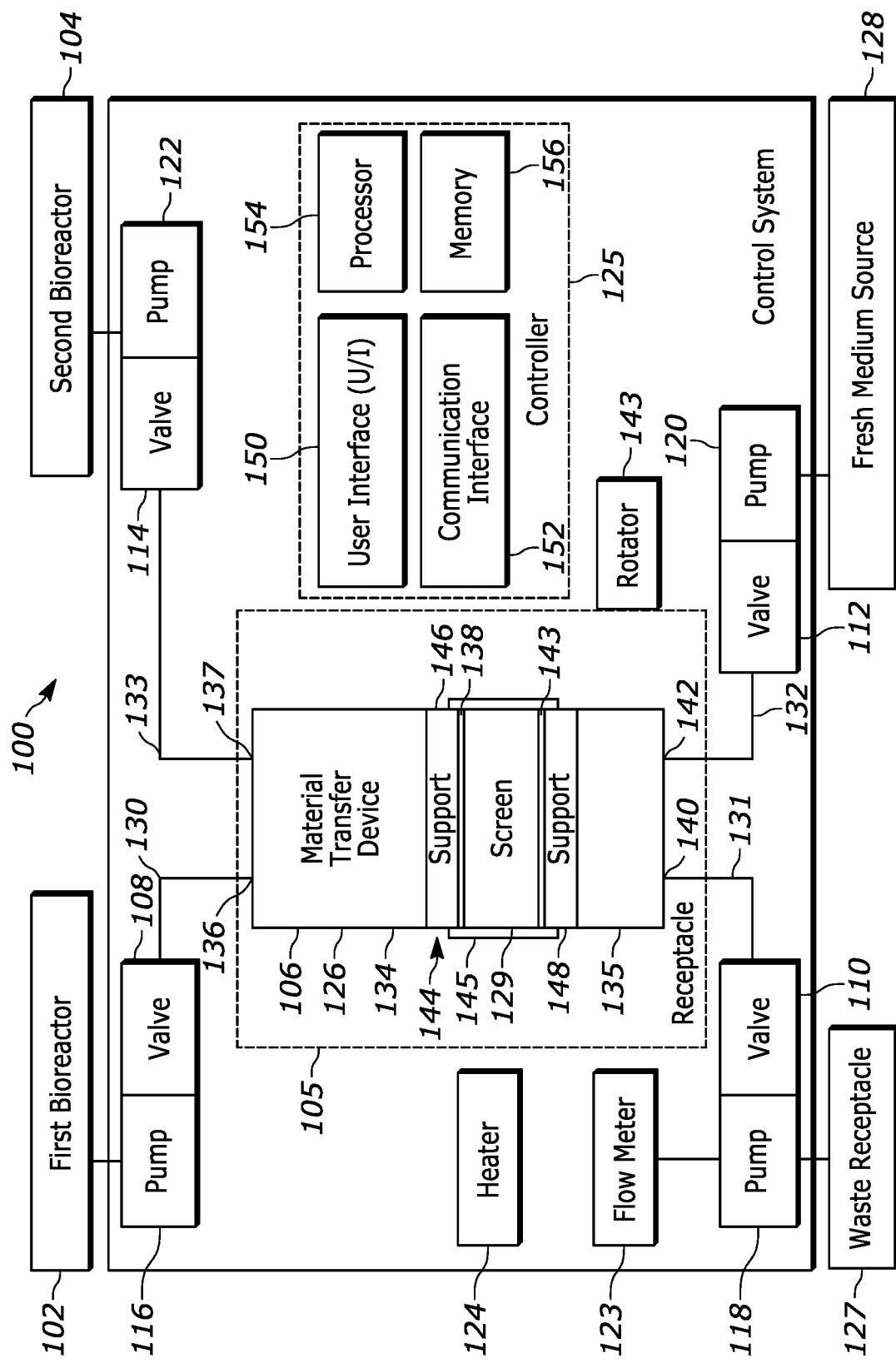
FIG. 1 illustrates a schematic diagram of an example control system in accordance with the teachings of this disclosure.

Although the following text discloses a detailed description of example methods, apparatus and/or articles of manufacture, it should be understood that the legal scope of the property right is defined by the words of the claims set forth at the end of this patent. Accordingly, the following detailed description is to be construed as examples only and does not describe every possible example, as describing every possible example would be impractical, if not impossible. Numerous alternative examples could be implemented, using either current technology or technology developed after the filing date of this patent. It is envisioned that such alternative examples would still fall within the scope of the claims.

The example methodology, apparatus, and/or articles of manufacture are distinct from seemingly similar methods and devices that utilize a mesh filter to restrict MCs in fluid. Commercially available devices with porous mesh filters (such as a cell strainers) intend to trap MCs while allowing desired cells or cell products of interest to flow through the pores after detaching the cells from the MCs. The desired cells or products remain in the same fluid after passing through the filter while the MCs are collected on one side of the filter and subsequently discarded. Typically, cells are detached from the surface of the MCs before entering the device and pore size is selected in order to only restrict the MCs from passing through. Alternatively, cells can remain attached to the surface of MCs if the purpose of the cells is to produce proteins or similar cell-based products that then are intended to pass through the mesh; the MCs with attached cells are still discarded together. Aggregates of therapeutic cells are typically similar or even larger in size than MCs. However, because the cells themselves are the desired product, cell aggregates need to be recovered during the medium exchange process and cannot be treated in the same manner as discardable MCs in a cell retention device.

In contrast, the following example methodology, apparatus, and/or articles of manufacture distinguish themselves by retaining MCs or cell aggregates on one side of a mesh filter, and then recovering and transferring them by reversing the flow of new medium through the mesh filter into a new bioreactor that is filled and preconditioned with new medium. This process using the example device allows for rapid and complete medium exchange. As the therapeutic cells of interest are grown on the surface of MCs or as aggregates, they are not intended to be discarded in any way. Rather, MCs with cells grown on its surface or cell aggregates enter an example device (external to a cell culture device such as a bioreactor) in spent medium, then are collected and recovered on one side of a mesh filter. Only undesired spent medium quickly flows through the filter and is discarded as waste. At a predetermined point, fresh medium flows from the opposite side of the filter (same as the waste side) in order to dislodge MCs and aggregates from the filter pores and suspend them in new medium. The fresh medium containing MCs with desired cells grown on its surface or as aggregates exits the example device, from the opposite side of the mesh as the waste side, to a new bioreactor filled and preconditioned with new medium.

In addition, in order to promote complete recovery of MCs or cell aggregates, the device may be rotated to allow the MCs or aggregates to fall down from the mesh filter due to gravity during the reverse medium flow. This can be performed rapidly before fresh medium has been introduced into the device in order to ensure that complete medium exchange occurs. Furthermore, the rotatable device may also incorporate a heating element to minimize any temperature difference the cells experience in the brief time they are not suspended in heated medium.

FIG. 1 illustrates a schematic diagram of an example control system 100 in accordance with the teachings of this disclosure. The control system 100 can be used to transfer cell aggregates or microcarriers (MCs) from a first bioreactor 102 to a second bioreactor 104. The control system 100 may also be used to transfer MCs from one or more first bioreactors to one or more second bioreactors. The MCs may be suspended in a medium which may be replaced by the control system 100.

In the example shown, the control system 100 includes a receptacle 105 to receive or otherwise carry a material transfer device 106 and includes, in part, a plurality of valves 108, 110, 112, 114, a plurality of pumps 116, 118, 120, 122, a flow meter 123, a heater 124, and a controller 125. In some implementations, the first bioreactor 102, the material transfer device 106, and the second bioreactor 104 is a closed system that provides an aseptic environment. The aseptic environment may be a sterile environment that is free from contaminants, etc. The controller 125 is electrically and/or communicatively coupled to the valves 108, 110, 112, 114, the pumps 116, 118, 120, 122, the flow meter 123, and the heater 124 and is adapted to cause the valves 108, 110, 112, 114, the pumps 116, 118, 120, 122, the flow meter 123, and the heater 124 to perform various functions as disclosed herein. The valves 108-114 may be pinch valves and the pumps 116-122 may be peristaltic pumps. However, other types of valves may prove suitable, other types of pumps may prove suitable, and/or one or more of the valves 108-114 and/or the pumps 116-122 may be omitted as further discussed below.

The material transfer device 106 and the valves 108-112 act as a four-way fluid control device that controls the flow of spent medium through a housing 126 of the material transfer device 106 and between the first bioreactor 102 to a waste receptacle 127 and controls the flow of fresh medium from a fresh medium source 128, through the housing 126 of the material transfer device 106 to the second bioreactor 104. The pumps 116, 118, 120, 122 are used to pump the medium, spent or fresh, through fluidic tubes 130, 131, 132, 133 that fluidly couple the material transfer device 106 and the first bioreactor 102, the waste receptacle 127, the fresh medium source 128, and the second bioreactor 104.

In the example shown, the material transfer device 106 includes a screen 129 disposed between first and second portions 134, 135 of the housing 126. The housing portions 134 and/or 135 may be removably coupled to each other or integrally formed together, and may each be rigid structures, semi-rigid structures, and/or made of a flexible material.

The first housing portion 134 includes a first inlet port 136, a first outlet port 137, and a first transfer opening 138 and, similarly, the second housing portion 135 includes a second outlet port 140, a second inlet port 142, and a second transfer opening 143 that is adjacent to and in communication with the first transfer opening 138. As a result of the communication between the transfer openings 138, 143, fluid (e.g., medium) can flow between the first and second transfer openings 138, 143 and through the screen 129 adjacent to the first and second transfer openings 138, 143.

In embodiments where the first and second housing portions 134, 135 are removable coupled together, a seal 145 may be disposed at an interface between the first housing portion 134 and the second housing portion 135 to prevent fluid from leaking out of the housing 126. The seal 145 may be an external seal that wraps around the housing 126 at the interface between the housing portions 134, 135. Additionally, in such versions, the housing portions 134, 135 can be coupled together with one or more fasteners, clamps, magnets, etc.

During a MC transfer/medium exchange process, the valves 108, 110 may be open and the pump 116 may pump spent medium including MCs through the first inlet port 136 and into the first housing portion 134. The screen 129 allows the spent medium to pass through the screen 129 into the second housing portion 135 and prevents the MCs from passing through the screen 129. The spent medium may flow into the second housing portion 138 based on gravity or based on a fill level of the spent medium within the housing 126 when, for example, the first housing portion 134 is beneath the second housing portion 135. As and/or after the spent medium collects in the second housing portion 135, the pump 118 may pump the spent medium from the second housing portion 135 and to the waste receptacle 127.

As the MCs collect on the screen 129, the flow rate of the spent medium into the second housing portion 135 and/or out of the material transfer device 106 may decrease. To compensate for a change in the flow rate through the screen 129, the controller 125 may change the pump rate of the pump 116. In an example, the flow meter 123 is used to determine a flow rate value of the spent medium exiting the second housing portion 135. The controller 125 may change a pump rate of the pump 116 in response to the determined flow rate value satisfying a threshold flowrate valve. Thus, the control system 100 may dynamically change the pump rates based on the flow rate into, through, and/or out of the material transfer device 106.

In some examples, after a threshold amount of the MCs has been collected on the screen 129 and/or after the spent medium has been pumped out of the second housing portion 135, the controller 125 may close the valves 108, 110, open the valves 112, 114 and cause the pump 120 to carry fresh medium through the second inlet port 142 and into the second housing portion 135 from the fresh medium source 128. As an alternative, the second inlet port 142 may be coupled to the first housing portion 134 and, thus, the fresh medium may directly flow into the first housing portion 134. The fresh medium entering the housing 124 may be preheated and/or the heater 124 may heat the fresh medium and/or contents of the material transfer device 106 to reduce temperature fluctuations that the MCs are exposed to. The heater 124 may heat a section of the housing 126 or the entire housing 126.

After the second housing portion 135 is filled with the fresh medium, the fresh medium passes through the screen 129 and re-suspends the MCs within the first housing portion 134 by, for example, dislodging the MCs from the screen 129. As and/or after the first housing portion 134 is filled with the fresh medium, the pump 122 may pump the fresh medium suspending the MCs through the first outlet port 137 and to the second bioreactor 104. The second bioreactor 104 may be preconditioned with fresh medium to allow any spent medium contained within the housing 126 after the pump 118 pumps the spent medium out of the material transfer device 106 to be diluted in the larger total volume of the second bioreactor 104. The controller 125 may thereafter close the valves 112, 114 and open the valves 108, 110 if additional MCs are to be transferred between the bioreactors 102, 104. While the above example discloses transferring MCs from one bioreactor to another, MCs may be transferred from one or more first bioreactors to one or more other second bioreactors. For example, MCs may be transferred from two bioreactors to a single bioreactor.

The first inlet port 136 and the first outlet port 137 may be arranged toward the top of the material transfer device 106, on the sides of the material transfer device 106, and/or toward the bottom of the material transfer device 106. When the first inlet port 136 and the first outlet port 137 are arranged toward the top of material transfer device 106, the MCs may accumulate on a top surface of the screen 129 and the spent medium may exit toward the bottom of the material transfer device 106. When the first inlet port 136 and the first outlet port 137 are arranged toward the bottom of material transfer device 106, the MCs may accumulate on a bottom surface of the screen 129 and/or otherwise in a lower portion of the housing 126 and the spent medium may exit toward the top of the material transfer device 106. Regardless of the orientation of the ports 136, 137, 140, 142, the control system 100 may flow fluid through the material transfer device 106 in either direction.

In some implementations, the control system 100 also includes a rotator 143 that is configured to rotate the material transfer device 106 to encourage the MCs to move away from the screen 129 and become resuspended. The rotator 143 may include a cradle defining the receptacle 105, actuators, etc. The cradle may be journaled to enable the cradle to move between the different positions.

While the above example mentions pumping fluid through the material transfer device 106 using the pumps 116-122, one or more of the pumps 116-122 may be omitted. If the pumps 116-122 are omitted, the MCs may be less likely of to become damaged in the transfer process. In such an example, the medium and/or the MCs may be moved based on a differential pressure between the material transfer device 106 and any of the external devices 102, 104, 127, 128. As an example, the first bioreactor 102 may be pressurized to flow spent medium containing MCs into the first housing portion 134 after the valve 108 is opened. As another example, the medium transfer device 106 may be pressurized to allow fresh medium containing the MCs to flow into the second bioreactor 104 after the valve 114 is opened. Other fluid flow options may prove suitable such as using gravity.

Referring again to the material transfer device 106, the material transfer device 106 includes a support 144 to provide structural support for the screen 129 and that is operably coupled to the housing 126 and disposed between the first and second housing portions 134, 135 and adjacent to the screen 129. In the example shown, the support 144 includes a first support 146 extending across the first transfer opening 138 and a second support 148 extending across the second transfer opening 143. The support 146 and/or 148 may include a lattice structure or another structure.

Referring to the controller 125, in the example shown, the controller 125 includes a user interface 150, a communication interface 152, one or more processors 154, and a memory 156 storing instructions executable by the one or more processors 154 to perform various functions including the disclosed examples. The user interface 150, the communication interface 152, and the memory 156 are electrically and/or communicatively coupled to the one or more processors 154.

In an example, the user interface 150 is adapted to receive input from a user such as a flow sequence desired and to provide information to the user associated with the operation of the control system 100. The input received may allow the controller 125 to customize a program that automates control of the valves 108, 110, 112, 114 and/or the pumps 116, 118, 120, and/or 122 depending on the desired flow sequence and/or material transfer device 106 being used. The user interface 150 may include a touch screen, a display, a keyboard, a speaker(s), a mouse, a track ball, and/or a voice recognition system. The touch screen and/or the display may display a graphical user interface (GUI).

In an example, the communication interface 152 is adapted to enable communication between the control system 100 and a remote system(s) (e.g., computers) via a network(s). The network(s) may include an intranet, a local-area network (LAN), a wide-area network (WAN), the intranet, etc. Some of the communications provided to the remote system may be associated with the flow sequence, transfer data, filtering data, flow rate data, etc., generated or otherwise obtained by the control system 100.

The one or more processors 154 and/or the control system 100 may include one or more of a processor-based system(s) or a microprocessor-based system(s). In some examples, the one or more processors 154 and/or the control system 100 includes a reduced-instruction set computer(s) (RISC), an application specific integrated circuit(s) (ASICs), a field programmable gate array(s) (FPGAs), a field programmable logic device(s) (FPLD(s)), a logic circuit(s), and/or another logic-based device executing various functions including the ones described herein.

The memory 156 can include one or more of a hard disk drive, a flash memory, a read-only memory (ROM), erasable programable read-only memory (EPROM), electrically erasable programable read-only memory (EEPROM), a random-access memory (RAM), non-volatile RAM (NVRAM) memory, a compact disk (CD), a digital versatile disk (DVD), a cache, and/or any other storage device or storage disk in which information is stored for any duration (e.g., permanently, temporarily, for extended periods of time, for buffering, for caching).

Figure 2:
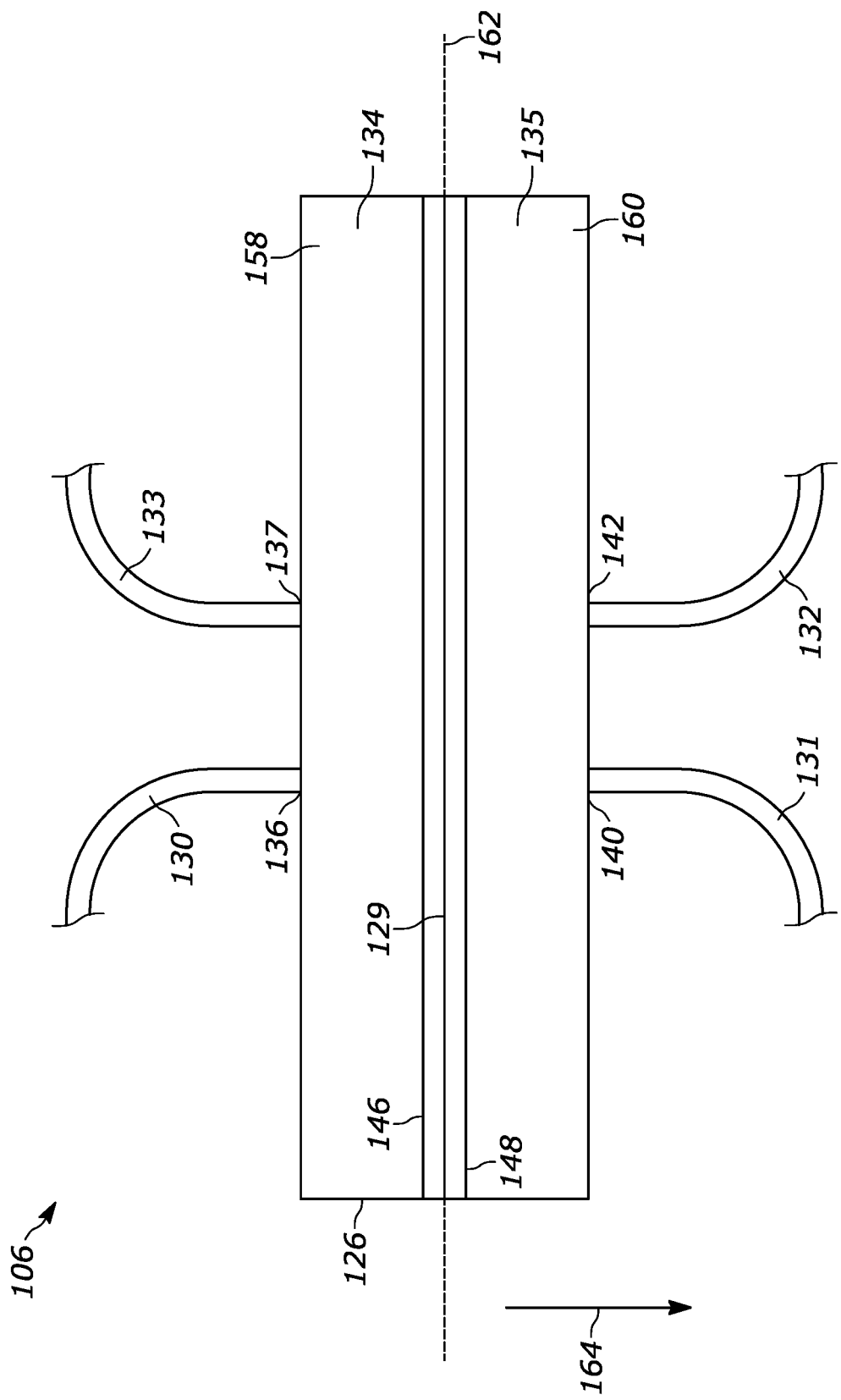
FIG. 2 is a cross-sectional view of an example of the material transfer device of FIG. 1.

FIG. 2 is a cross-sectional view of an example of the material transfer device 106 of FIG. 1. The material transfer device 106 may be a single-use device that is intended to maintain a closed system with the bioreactors 102, 104, the waste receptacle 127, and/or the fresh medium source 128 that the fluidic tubes 130, 131, 132, 133 will be aseptically connected to. In the example shown, the material transfer device 106 includes the first housing portion 134 oriented as an upper housing portion 158 and the second housing portion 135 oriented as a lower housing portion 160. The screen 129 is horizontally disposed (e.g., parallel) relative to a horizontal plane 162 and between the housing portions 134, 135. The supports 146, 148 are also horizontally disposed relative to the horizontal plane 162. Based on the orientation of the upper and lower housings 158, 160, the spent medium may flow through the material transfer device 106 in a direction generally indicated by arrow 164 based on gravity. However, alternatively, the spent medium may flow through the material transfer device 106 in a direction generally opposite the direction generally indicated by arrow 164. Moreover, the upper and lower housings 158, 160 and/or screen 129 may be differently oriented (see, for example, FIGS. 4 and 5).

Still referring to the example of FIG. 2, the first inlet port 136 and the first outlet port 137 are centrally disposed in the first housing portion 134 and the second outlet port 140 and the second inlet port 142 are centrally disposed in the second housing portion 135. However, any one of the ports 136, 137, 140, 142 may be differently arranged. For example, the ports 136, 140, 142 may have axes that are parallel to a central plane of the material transfer device 106 (see, for example, FIGS. 4 and 5).

Figure 3:
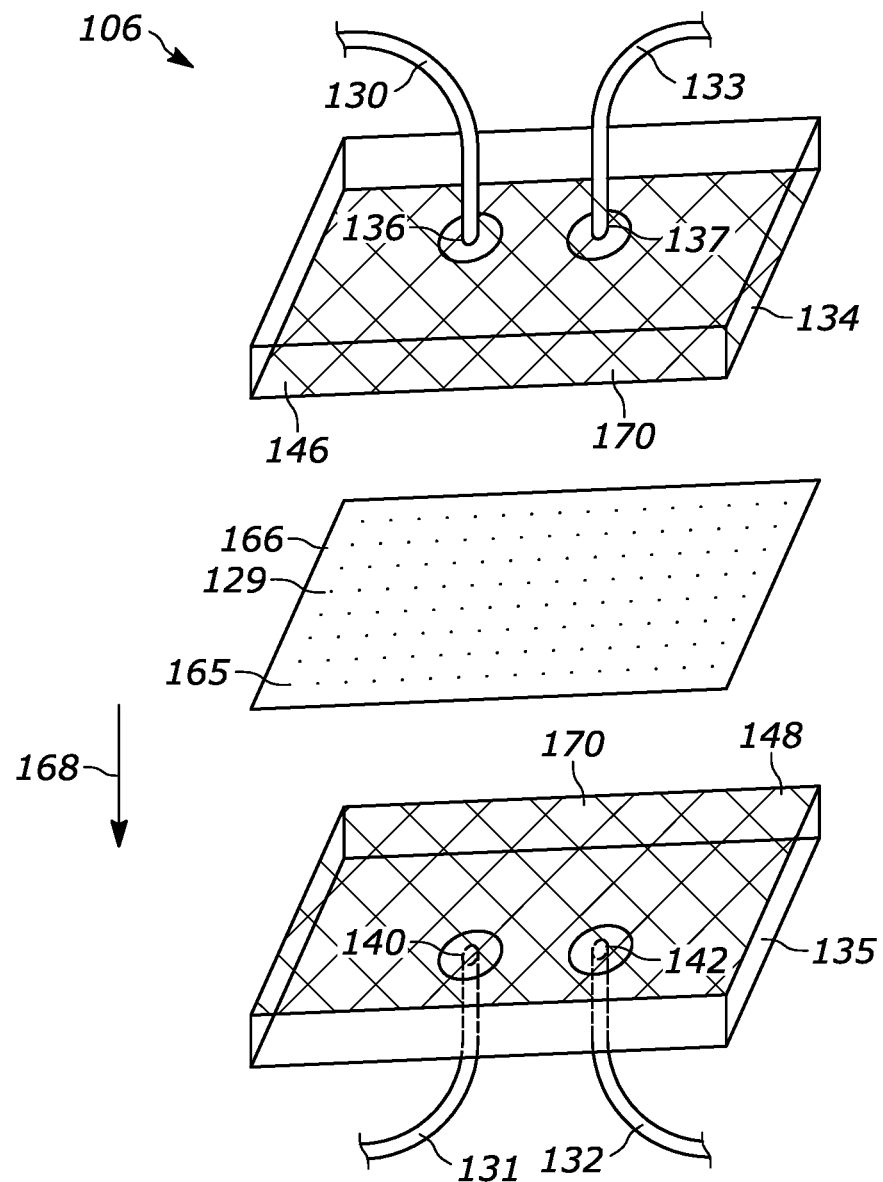
FIG. 3 is an expanded view of the material transfer device of FIG. 2.

FIG. 3 is an expanded view of the material transfer device 106 of FIG. 2. In the example shown, the screen 129 includes a plurality of pores 165 that allow the flow of the medium therethrough but filter out the MCs. The pores 165 allow the MCs to accumulate on an upper surface 166 of the screen 129 as the spent medium flows through the screen 129 in a direction generally indicated by arrow 168 and/or as the fresh medium flows through the screen 129 in a direction generally opposite to the direction indicated by the arrow 168 to rehydrate the MCs. Each of the pores 165 may be the same size or some or all of the pores 165 may be different sizes. A size of the pores 165 may correspond to the MCs being filtered. In an example, the pores 165 are between about 70 microns ($\mu$m) and about 75 $\mu$m.

The supports 146, 148 may be formed as a lattice structure 170 that are adapted to provide structural support on both sides of screen 129 (e.g., top and bottom) to reduce the likelihood that the screen 129 bows and/or sags in response to the medium flowing through the screen 129 and/or a weight of the MCs accumulating on the screen 129. The supports 146, 148 and/or the associated lattice structure 170 may be arranged to reduce the number of pores 165 that are blocked by the structures 146, 148, and/or 170. Thus, more of the medium can freely pass through the screen 129 in the direction generally indicated by arrow 168 and/or in the direction generally opposite the direction indicated by arrow 168. In an example, the screen 129 may include a number of the pores that takes into account a number of the pores 165 that may become clogged with the MCs and the number of pores 165 that may remain unclogged, allowing for the liquid to rapidly flow through the pores 165.

Figure 4:
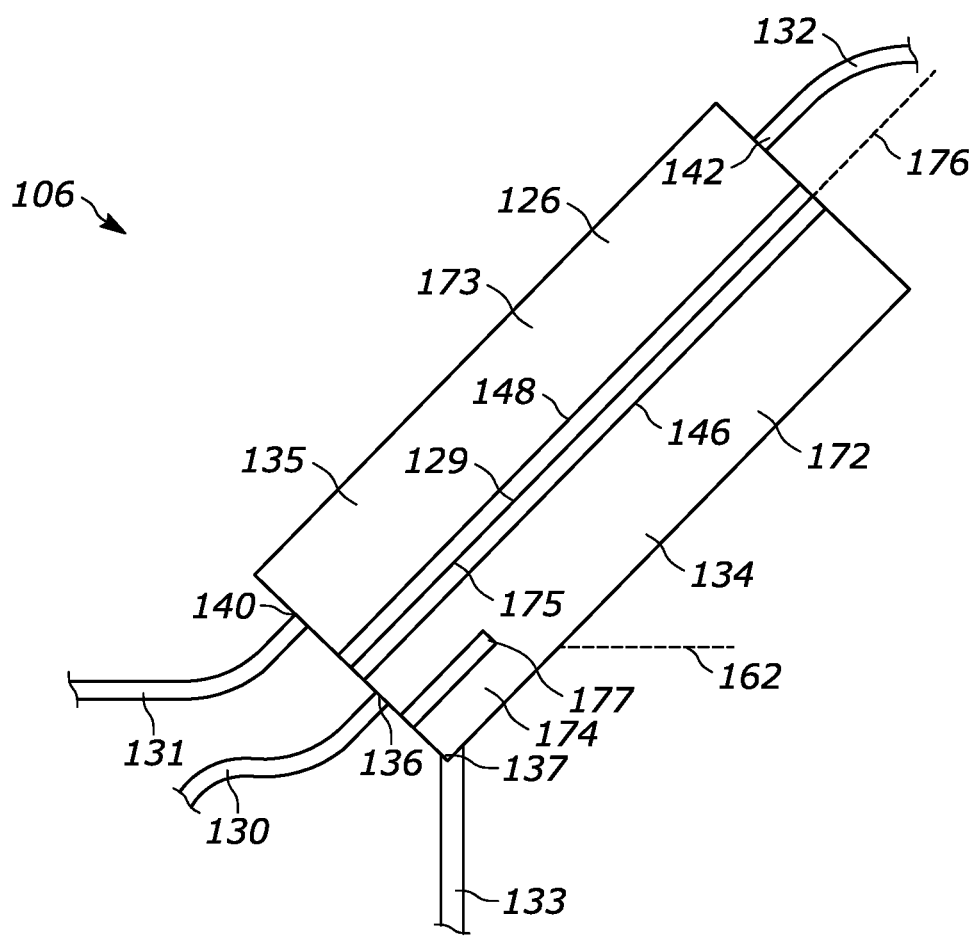
FIG. 4 is a cross-sectional view of another example of the material transfer device of FIG. 1.

FIG. 4 is a cross-sectional view of another example of the material transfer device 106 of FIG. 1. The housing 126, the screen 129, and the supports 146, 148 of the material transfer device 106 of FIG. 4 are similar to the housing 126, the screen 129, and the supports 146, 148 of the material transfer device 106 of FIG. 2. However, in contrast to the material transfer device of FIG. 2, the ports 136, 137, 140, 142 of the material transfer device 106 of FIG. 4 are differently arranged and the first housing portion 134 is oriented as a lower housing portion 172 and the second housing portion 135 is oriented as an upper housing portion 173. However, as discussed above, any of the ports 136, 137, 140, 142 may be used to introduce spent medium into the material transfer device 106 and any of the ports 136, 137, 140, 142 may be used to introduce fresh medium into the material transfer device 106.

In some examples, axes some of the ports 136, 140, 142 are disposed approximately parallel to a central plane 176 of the material transfer device 106, with the first inlet port 136 being arranged higher than the first outlet port 137 and the second outlet port 140 being arranged lower than the second inlet port 142. In the example shown, the screen 129 and the housing 126 is disposed at an angle relative to the horizontal plane 162 when the material transfer device 106 is being used. However, the screen 129 and the housing 126 may be arranged in different orientations.

In operation, the first inlet port 136 flows the spent medium including the MCs into the first housing portion 134 and tangentially along a surface 175 of the screen 129. The spent medium passes through the screen 129 into the second housing portion 135 and out of the second outlet port 140. A funnel shaped portion 174 of the first housing portion 134 leads to the first outlet port 137 and is arranged to accumulate MCs within the first housing portion 134. In the example shown, the first housing portion 134 includes an internal barrier 177 that extends across a width of the first housing portion 134 and is adapted to prevent MCs that accumulate in the funnel shaped portion 174 from covering the first inlet port 136 of the first housing portion 134. The internal barrier 177 may alternatively extend over a portion of the width of the first housing portion 134 and/or the internal barrier 177 may be omitted.

Figure 5:
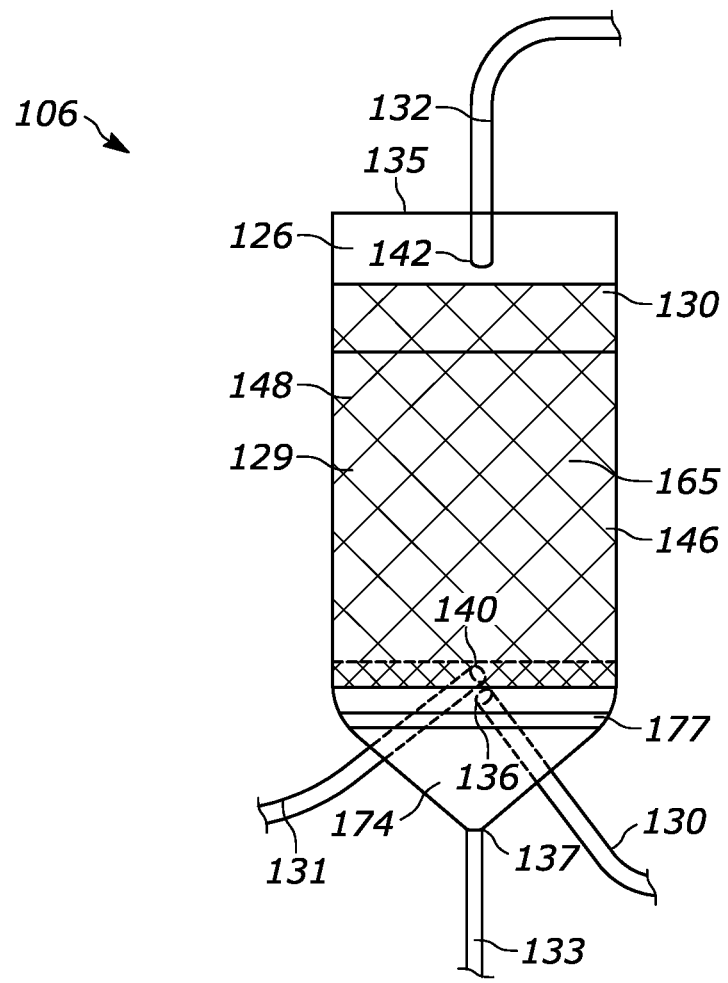
FIG. 5 is a front view of the material transfer device of FIG. 4 showing the funnel shaped portion of the first housing portion.

FIG. 5 is a front view of the material transfer device 106 of FIG. 4 showing the funnel shaped portion 174 of the first housing portion 134. The fluidic tubes 130, 131, 132, 133 are shown toward the bottom of the material transfer device 106 and the fluidic tube 132 is shown toward the top of the material transfer device 106.

Figure 6:
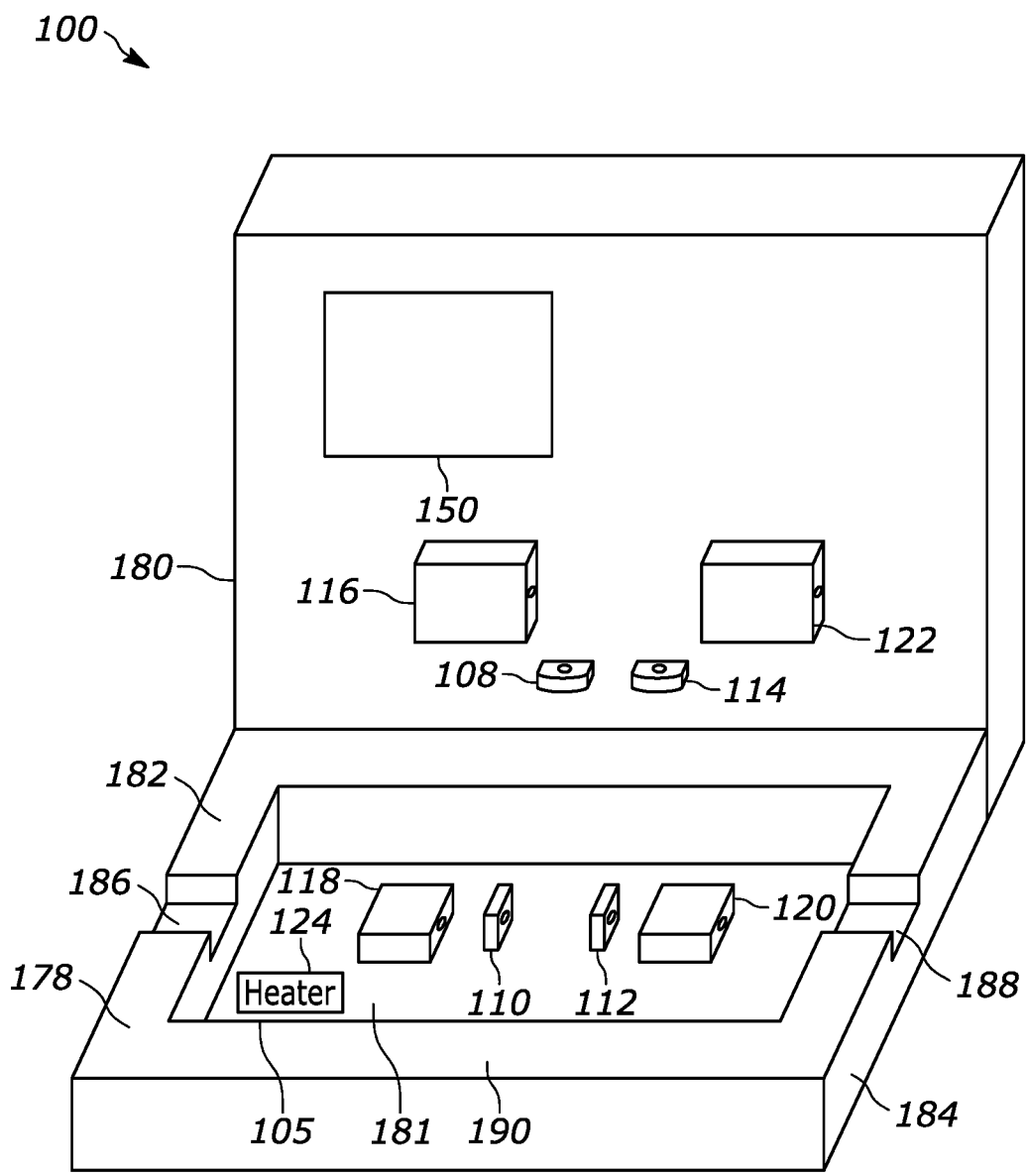
FIG. 6 is an isometric view of an example of the control system of FIG. 1.

FIG. 6 is an isometric view of an example of the control system 100 of FIG. 1. In the example shown, the control system 100 includes a base 178 defining the receptacle 105 and carrying two of the valves 110, 112 and two of the corresponding pumps 118, 120 and a wall 180 coupled to the base 178 and carrying two of the valves 108, 114 and two of the corresponding pumps 116, 122. The base 178 includes the receptacle 105 having a recessed area 181 that provides space for the fluidic tubes 131, 132 to bend from the material transfer device 106 and be coupled to the corresponding valves 110 and/or 112 and/or the pumps 118 and/or 120. The heater 124 is shown being disposed within the recessed area 181. However, the heater 124 may be in a different location and still be arranged to maintain the MCs within the material transfer device 106 at a relatively consistent temperature. The base 178 also includes a first side 182 opposite a second side 184, with each side 182, 184 defining a channel 186, 188 through which at least one of the fluidic tubes 131, 132 passes.

Figure 7:
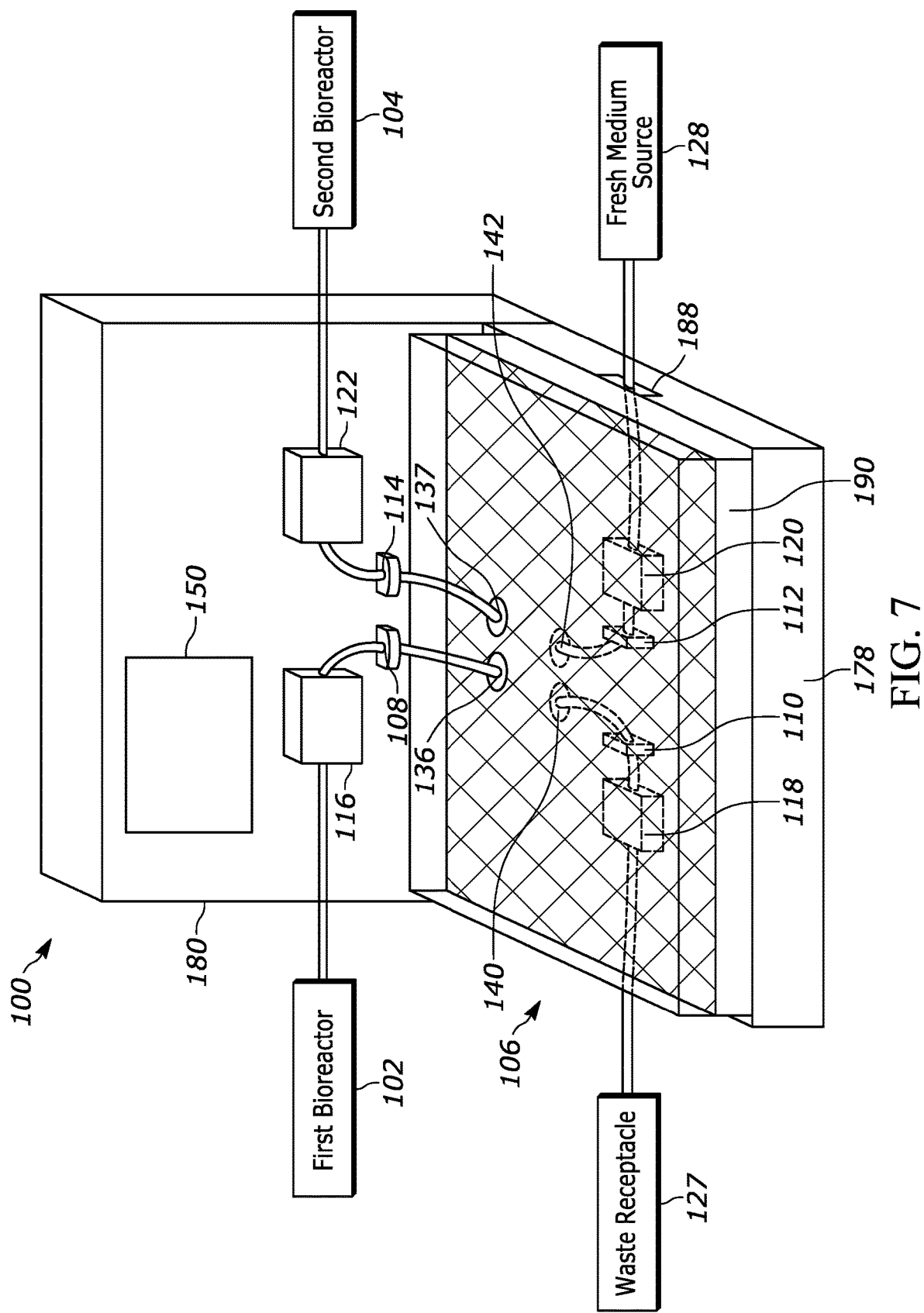
FIG. 7 is an isometric view of the control system of FIG. 6 with the material transfer device disposed within the receptacle and/or resting on a top surface of the base.

FIG. 7 is an isometric view of the control system 100 with the material transfer device 106 disposed within the receptacle 105 and/or resting on a top surface 190 of the base 178. In operation, the control system 100 may actuate one or more of the valves 108, 110, 112, 114 and/or the pumps 116, 118, 120, 122 to replace spent medium with fresh medium and transfer the MCs between the first and second bioreactors 102, 104. While FIG. 7 illustrates the bioreactors 102, 104, the waste receptacle 127, and the fresh medium source 128 coupled to the corresponding ports 136, 137, 140, 142, the bioreactors 102, 104 may be coupled to the ports 140, 142 and waste receptacle 127 and the fresh medium source 128 may be coupled to the ports 136, 137. In such an arrangement, the medium carrying the MCs may enter and exit the material transfer device 106 from the bottom of the material transfer device 106 and the medium not carrying the MCs may enter and exit the material transfer device 106 from the top of the material transfer device 106.

Further, while several examples have been disclosed herein, any features from any examples may be combined with or replaced by other features from other examples. Moreover, while several examples have been disclosed herein, changes may be made to the disclosed examples without departing from the scope of the claims.

What is claimed is:

1. A method of using a material transfer device including a first housing portion and a second housing portion with a screen disposed between the housing portions, each of the housing portions including an inlet port, an outlet port, and corresponding fluidic tubes connected to the inlet and outlet ports, the method comprising:
    transferring cell aggregates or microcarriers suspended in spent medium through the inlet port of the first housing portion;
    supporting the screen using a support operably coupled to at least one of the first and second housing portions and disposed between the first and second housing portions;
    filtering the cell aggregates or the microcarriers using the screen by passing all of the spent medium through the screen and into the second housing portion, all of the cell aggregates or all of the microcarriers being retained within the first housing portion after all of the spent medium passes through the screen;
    transferring the spent medium out of the outlet port of the second housing portion; and
    transferring fresh medium into the first housing portion;
    resuspending the cell aggregates or the microcarriers in the fresh medium in the first housing portion; and
    transferring the cell aggregates or the microcarriers suspended in the fresh medium out of the outlet port of the first housing portion.

2. The method of claim 1, wherein passing the spent medium through the screen includes passing the spent medium through a first transfer opening of the first housing portion and a second transfer opening of the second housing portion disposed adjacent to and in communication with the first transfer opening.

3. The method of claim 1, wherein passing the spent medium through the screen includes passing the spent medium through the screen horizontally disposed relative to a horizontal plane.

4. The method of claim 1, wherein passing the spent medium through the screen includes passing the spent medium through the screen disposed at an angle relative to a horizontal plane.

5. The method of claim 1, wherein transferring fresh medium into the first housing portion or the second housing portion comprises transferring the fresh medium into the second housing portion and passing the fresh medium through the screen into the first housing portion.

6. The method of claim 1, wherein at least part of the first housing portion is disposed below at least part of the screen.

7. The method of claim 1, wherein the first housing portion is disposed entirely below the screen.

8. The method of claim 1, wherein at least part of the first housing portion is disposed below at least part of the second housing portion.

9. The method of claim 1, wherein the first housing portion is disposed entirely below the second housing portion.

10. The method of claim 1, wherein transferring the spent medium including the cell aggregates or the microcarriers through the inlet port of the first housing portion comprises:
    (a) pumping the cell aggregates or the microcarriers in the spent medium to the material transfer device,
    (b) flowing the cell aggregates or the microcarriers in the spent medium to the material transfer device based on gravity, or
    (c) flowing the cell aggregates or the microcarriers in the spent medium to the material transfer device based on a pressure differential between a first bioreactor and the material transfer device.

11. The method of claim 1, further comprising heating the fresh medium being transferred into the first housing portion or the second housing portion.

12. The method of claim 1, further comprising heating the material transfer device.

13. The method of claim 1, further comprising rotating the material transfer device to encourage the cell aggregates or the microcarriers to move away from the screen and become resuspended.

14. The method of claim 1, further comprising inhibiting leaks from between the first housing portion and the second housing portion using a seal disposed at an interface between the first housing portion and the second housing portion.

15. The method of claim 1, further comprising changing a pump rate in response to a flow rate of the spent medium through the screen satisfying a threshold value.

16. The method of claim 1, wherein transferring the spent medium including the cell aggregates or the microcarriers through the inlet port of the first housing portion comprises transferring the spent medium including the cell aggregates or the microcarriers from a first bioreactor through the inlet port of the first housing portion and wherein transferring the cell aggregates or the microcarriers suspended in the fresh medium out of the outlet port of the first housing portion comprises transferring the cell aggregates or the microcarriers suspended in the fresh medium out of the outlet port of the first housing portion and into the first bioreactor or a second bioreactor different from the first bioreactor.

* * * * *